United States Patent [19]
Stephens et al.

[11] Patent Number: 5,607,397
[45] Date of Patent: Mar. 4, 1997

[54] ADAPTOR CAP AND TROCAR ASSEMBLY

[75] Inventors: Randy R. Stephens, Fairfield; Renato Roxas, Mason; Gregory C. Groenke, Loveland, all of Ohio

[73] Assignee: Ethicon, Inc., Somerville, N.J.

[21] Appl. No.: 279,780

[22] Filed: Jul. 25, 1994

Related U.S. Application Data

[63] Continuation of Ser. No. 284,453, Mar. 9, 1993, Pat. No. 5,338,307.

[51] Int. Cl.⁶ .................................................. A61M 5/178
[52] U.S. Cl. ............................................ 604/167; 604/256
[58] Field of Search ................................. 604/164, 167, 604/256, 264

[56] References Cited

U.S. PATENT DOCUMENTS

| | | | |
|---|---|---|---|
| 4,112,932 | 9/1978 | Chiulli | 128/3 |
| 4,715,360 | 12/1987 | Akui et al. | 604/256 |
| 5,057,093 | 10/1991 | Clegg et al. | 604/256 |
| 5,104,383 | 4/1992 | Shichman | 604/167 |
| 5,211,633 | 5/1993 | Stouder | 604/256 |
| 5,224,930 | 7/1993 | Spaeth et al. | 604/33 |
| 5,300,035 | 5/1994 | Clement | 604/167 |
| 5,312,362 | 5/1994 | Pfolsgraf | 604/256 |
| 5,407,433 | 4/1995 | Loomas | 604/167 |
| 5,437,646 | 8/1995 | Hunt et al. | 604/167 |

FOREIGN PATENT DOCUMENTS

WO93/04717  3/1993  WIPO .................... A61M 5/178

Primary Examiner—Todd E. Manahan
Attorney, Agent, or Firm—Paul A. Coletti

[57] ABSTRACT

An adaptor cap assembly is provided for a trocar, consisting of a base which contains an opening which is the same size as the opening of the trocar cannula handle. There is also a cap integrally attached to the base which contains a gasketing assembly wherein the assembly is of a smaller diameter than the diameter of the trocar cannula handle opening as well as the opening in the base of the adaptor cap assembly. This cap is hingedly attached to the base so that it can be flipped by using the thumb either into or out of alignment with the openings of the trocar cannula handle and the base of the adaptor cap assembly. Thus, this mechanism can be used so that a smaller diameter instrument can be placed within a larger diameter opening (with the adaptor cap in place), or, the adaptor cap can be moved out of place so that a larger diameter mechanism can be inserted within the adaptor cap assembly and into the trocar cannula handle, with both the base and the trocar cannula handle having the same size opening.

14 Claims, 5 Drawing Sheets

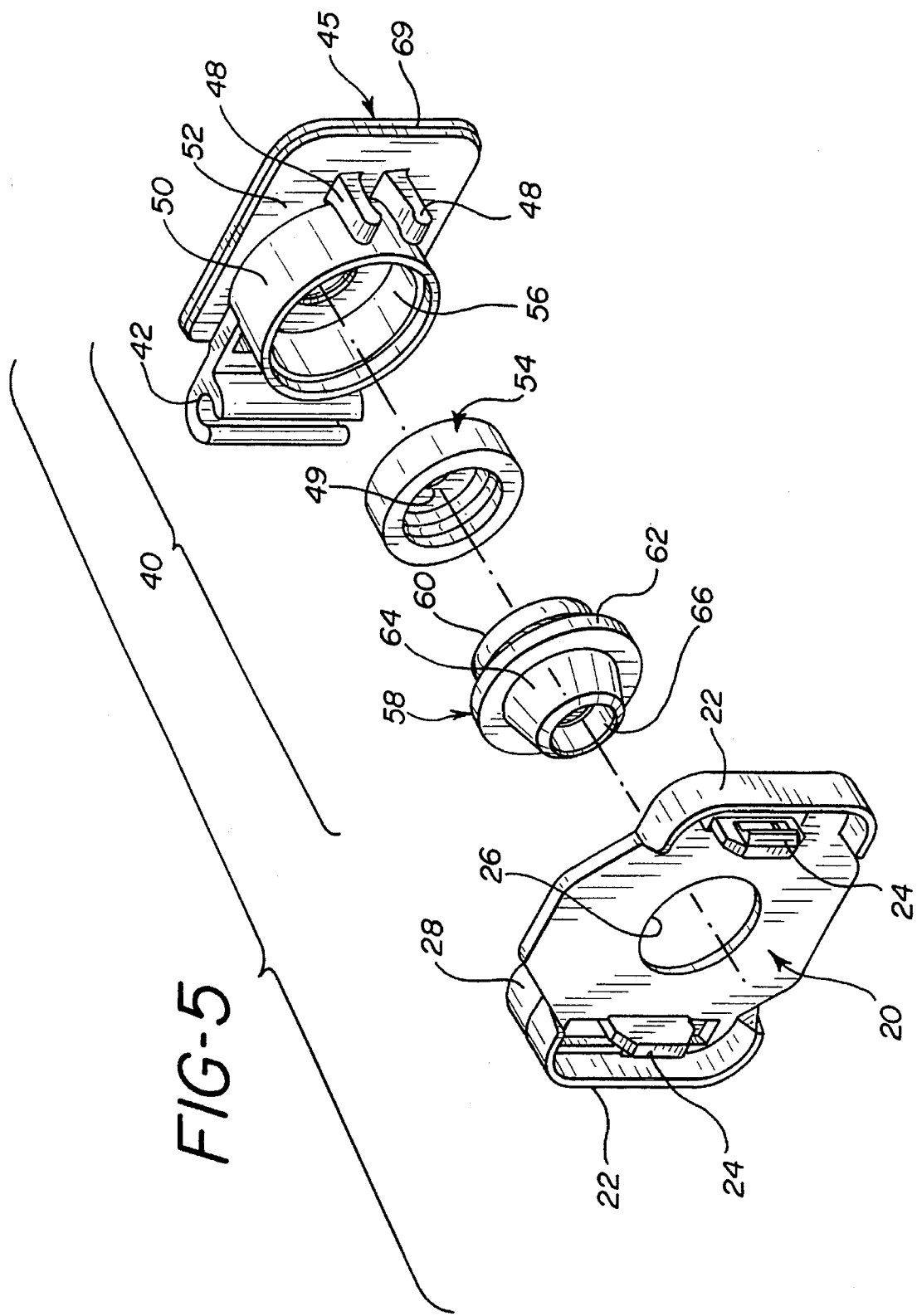

ADAPTOR CAP AND TROCAR ASSEMBLY

This is a continuation of application Ser. No. 08/028,453, filed Mar. 9, 1993, now U.S. Pat. No. 5,338,307 which is hereby incorporated by reference.

FIELD OF THE INVENTION

This invention concerns laparoscopic trocar assemblies. More particularly, this invention concerns an assembly which is attached to a trocar, and contains a mechanism for converting the opening to the trocar cannula from one diameter to another.

BACKGROUND OF THE INVENTION

With the rise in the use of laparoscopic surgery, it has been determined that there are additional needs necessary for operating a typical laparoscopic trocar. Specifically, it has been noticed that it may be desirable to convert the outer opening of the trocar cannula from a larger diameter to a smaller diameter. This smaller opening creates a seal about smaller diameter instruments used after puncturing the trocar with a laparoscopic obturator. Exemplary of such valving "reducer" mechanisms are Ser. No. 618,325, now U.S. Pat. No. D-335,536, assigned to Ethicon, Inc., and Ser. No. 877,903, filed May 1, 1992, now abandoned, similarly assigned to Ethicon, Inc., the assignee of the present invention. Each of these patent and patent application is herein incorporated by reference.

Also, there have been placed in the market products such as the Origin trocar, produced by Origin Medisystems of Palo Alto, California which contains an integral reducer cap, allowing a 10 mm opening to be converted to a 7 mm opening or a 5 mm opening. Such a system uses an integral sliding mechanism, which allows the seal to be rotated about a corner of the trocar cannula handle and emplaced over the 10 mm opening created in the obturator handle. However, this arrangement is quite cumbersome for surgeons. This is so because the sliding mechanics of the seals make it such that the seals are incapable of being rapidly and easily put into place. The user must move his or her thumb from the side of the instrument and around the top of the cannula handle over the opening in the cannula handle. This can be quite a tricky one handed maneuver.

What is desirable therefore is a reducer system which allows the user to rapidly and easily place the reduced opening in the reducer system over the opening of the trocar cannula. Also, it is an object of the invention to provide an integral system wherein there is no need to search on the surgical stand for a reducer. It is desirable, that is, to have the reducer attached at all times to the trocar cannula handle. Finally, it is an object of this invention to allow the user to convert the system not only from a larger diameter opening to a smaller diameter opening in a easy and readily operable fashion, but also to convert from a smaller opening to the larger opening in a similar easily operable and manageable fashion.

SUMMARY OF THE INVENTION

These and other objects of this invention are disclosed in a adaptor cap assembly for a trocar. The assembly consists of a base which contains an opening which is the same size as the opening of the trocar cannula handle. There is a cap integrally attached to the base which contains a gasketing assembly wherein the assembly contains an opening which is of a smaller diameter than the diameter of the trocar cannula handle opening as well as the opening in the base of the adaptor cap assembly. This cap is hingedly attached to the base so that it can be flipped by using the thumb either, into or out of alignment with the openings of the trocar cannula handle and the base of the adaptor cap assembly. Thus, this mechanism can be used so that a smaller diameter instrument can be placed within a larger diameter opening (with the adaptor cap in place), or, the adaptor cap can be moved out of place so that a larger diameter mechanism can be inserted within the adaptor cap assembly and into the trocar cannula handle, with both the base and the trocar cannula handle having the same size opening.

These and other aspects of the trocar adaptor cap assembly described by this invention will be better understood with reference to the Brief Description of the Drawings which follows taken in conjunction with the Detailed Description of the Invention.

BRIEF DESCRIPTION OF THE DRAWINGS

FIG. 5 is a perspective assembly drawing of the adaptor cap of this invention;

DETAILED DESCRIPTION OF THE INVENTION

Figure 1:
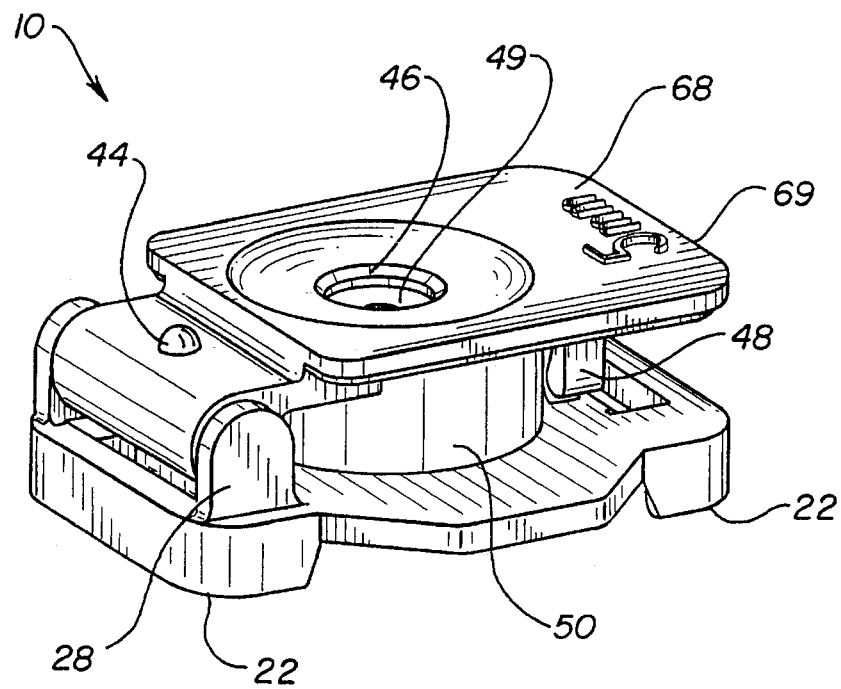
FIG. 1 is a perspective view of the adaptor cap of the present invention.

As seen in FIGS. 1–6, there is disclosed herein an adaptor cap assembly 10 useful with a trocar mechanism 100. The trocar mechanism 100 is better in phantom in FIGS. 7 and 7a. As seen in FIG. 7, the trocar mechanism 10 contains an obturator 105, which is inserted into a cannula 110. The cannula 110 is attached to the cannula handle 112. The obturator 105 is attached to an obturator handle 107 matable with cannula handle 112, as better described in U.S. Pat. No. 5,066,288 to Deniega, herein incorporated by reference.

Figure 6:
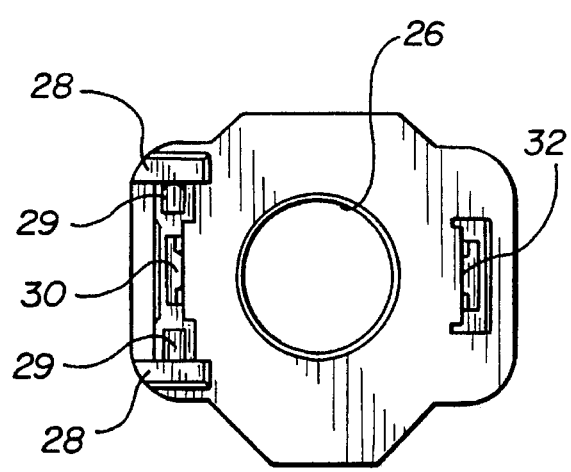
FIG. 6 is a plan view of the base of the adaptor cap with the outer gasket and insert of this adaptor cap removed.
Figure 7:
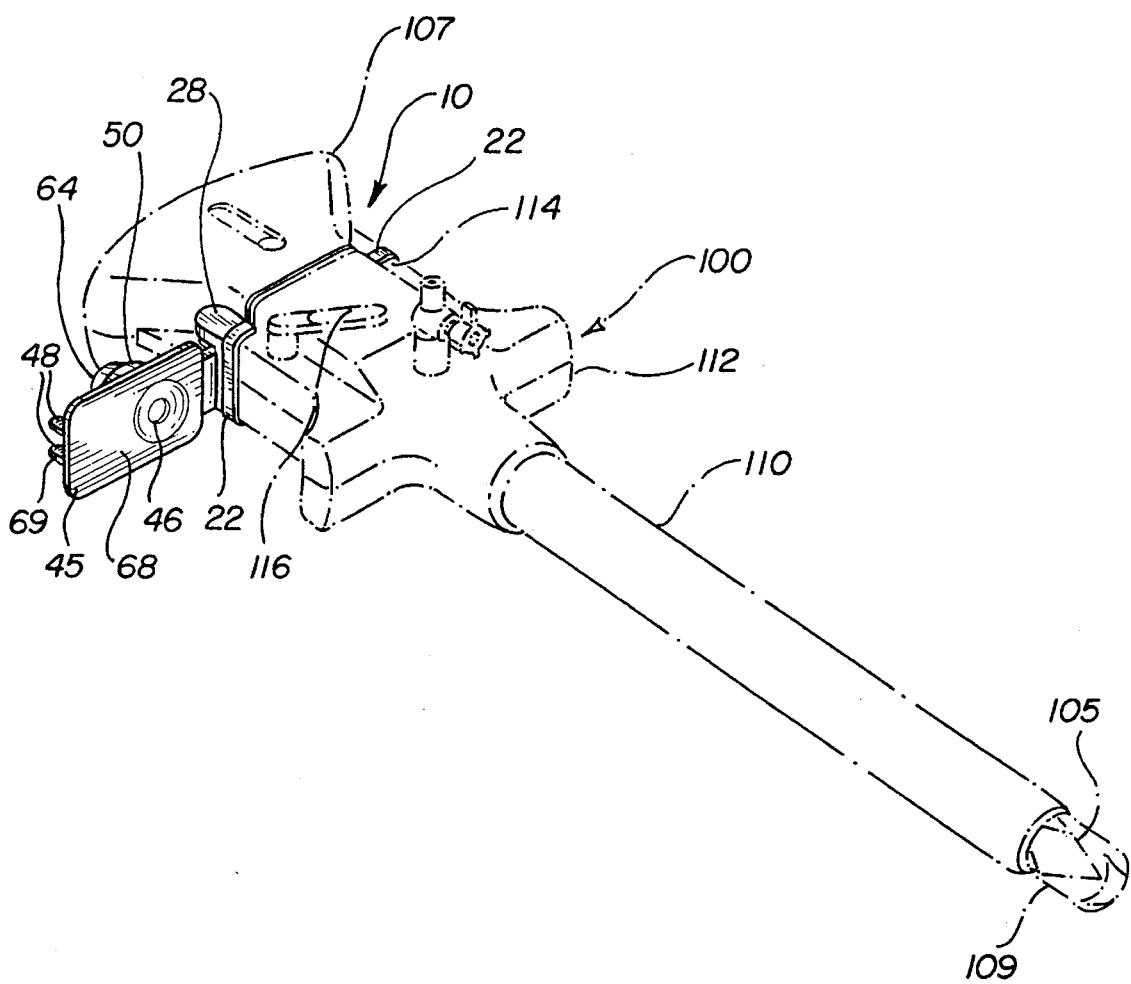
FIG. 7 is a perspective view of the adaptor cap placed on a trocar in the open position, with a trocar obturator placed therethrough.
Figure 7A:
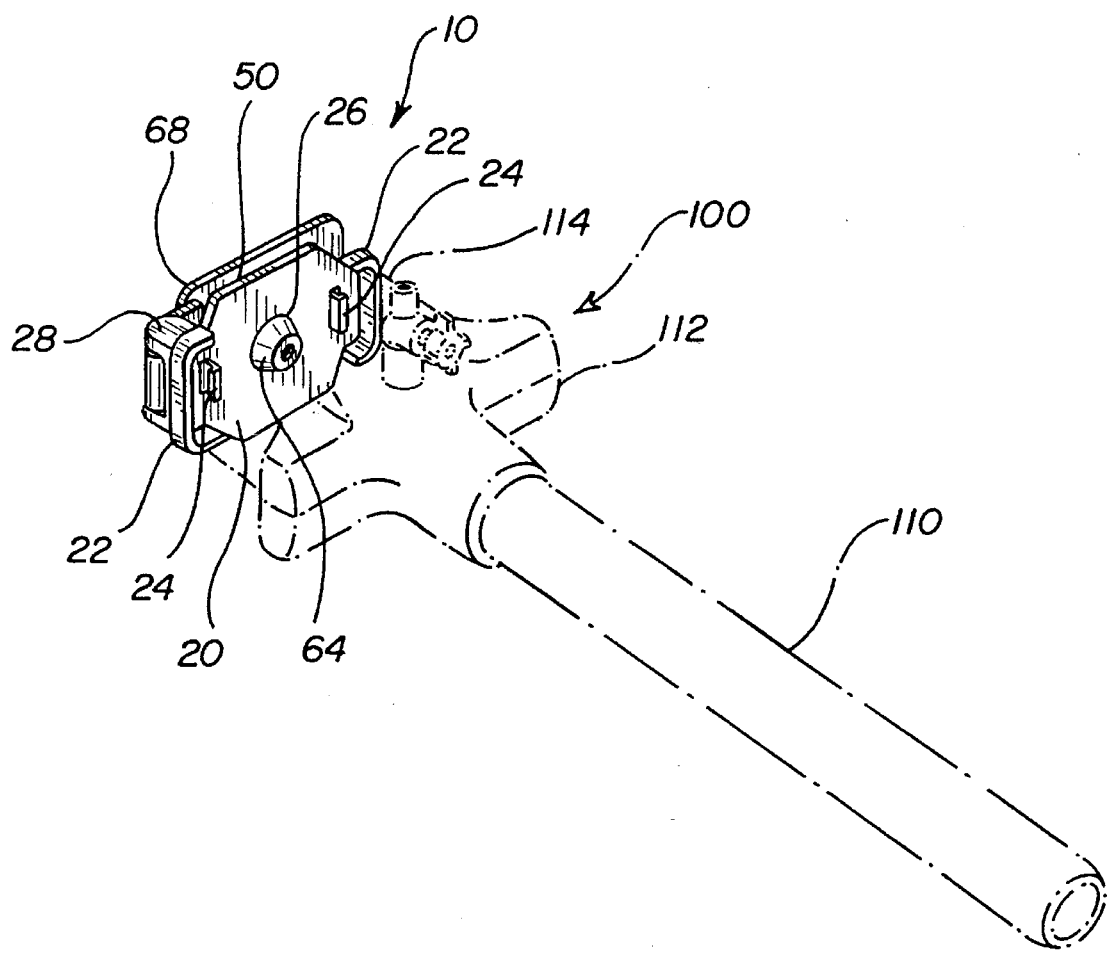
FIG. 7a is a perspective view of a closed adaptor cap placed over the same trocar as in FIG. 7, with the obturator and obturator handle removed from the trocar.

As seen in FIGS. 1, 5 and 7a, the adaptor cap assembly 10 of this invention contains a base 20 which on its underside has a flange 22 adapted to be placed around the proximal circumference 114 of the cannula handle 112 of a trocar. Furthermore, tabs 24 associated with the base 20 of the adaptor cap assembly 10 mate with the walls of the trocar assembly 100 much in the same fashion as the tabs located on the reducer cap described in Ser. No. 618,325, incorporated by reference above. Also, as better seen in FIG. 5 and 6, the base 20 of the assembly contains an opening 26. This opening 26 is generally is 10 mm in diameter, and is centered over the generally 10 mm diameter opening of the cannula handle 112 contained in the trocar of FIGS. 7 and 7a.

The top portion of the base 20 is better seen in FIGS. 1, 3, 4 and 6. The top portion of the base contains a pair of hinge posts 28 which mateably accept the hinges 42 contained on the outer gasket assembly 40, as will later be explained. Also, as best seen in FIG. 6, there is contained a slot 30 into which a locking detent 44 of the outer gasket assembly 40 is able to be rotated, for acceptance into the slot 30, thereby retaining the adaptor cap assembly in the open position as seen in FIG. 7. Finally, the top of the base contains a retaining knob or ball 32 (used interchangeably throughout this specification as better seen in FIG. 4 which is capable of accepting a mateable locking mechanism placed on the outer gasket assembly 40 of this adaptor cap assembly.

Figure 2:
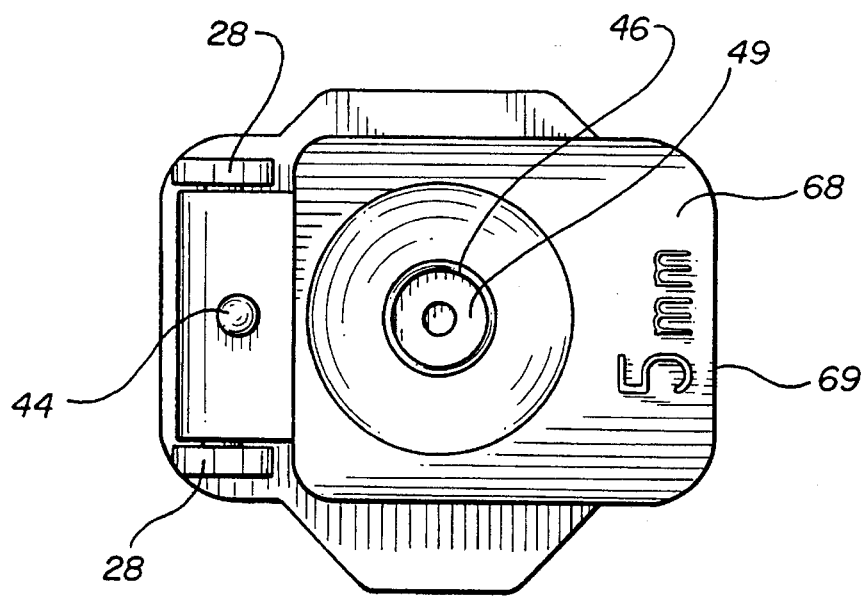
FIG. 2 is a plan view of the closed adaptor cap of the present invention.
Figure 3:
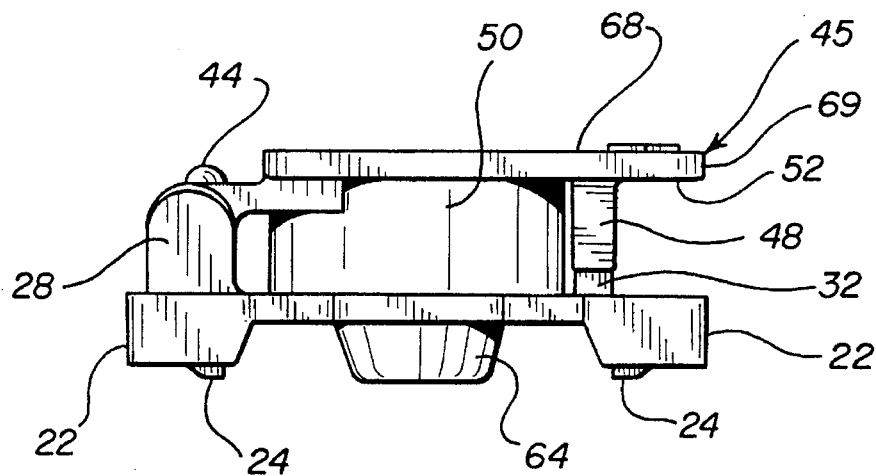
FIG. 3 is a front elevation view of the adaptor cap of the present invention.

The outer gasket assembly 40 is best seen in FIGS. 1, 2, 3, 4 and 5. As seen in FIGS. 1 and 2 the proximal or "upper" side of the outer gasket 45 contains a reduced diameter opening 46 with an elastomeric seal 49 contained therein. For instance, as presently configured this opening 46 is 5 mm in diameter. This opening 46 is centered over the opening 26 contained in the base 20 of the adaptor cap assembly 10 as best seen in FIGS. 2 and 5. Also, the proximal side of the outer gasket contains detent 44 as previously mentioned, which may be flipped so that it rests in the slot 30 contained in the base 20 to lock the outer gasket 45 into position as seen in FIG. 7.

Figure 4:
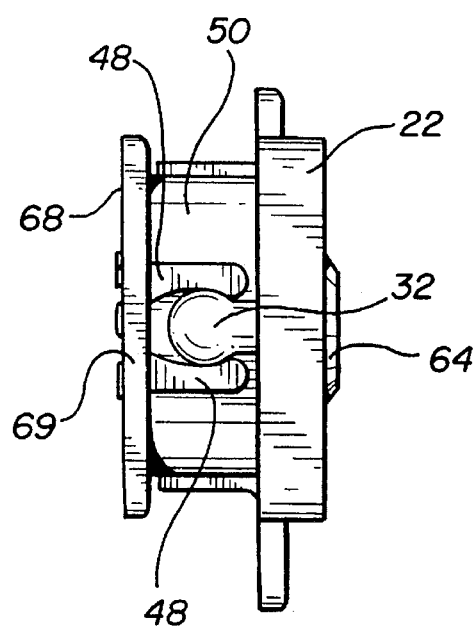
FIG. 4 is a side elevation view of the adaptor cap of the present invention, in the closed position.

On the distal or "underside" of the outer gasket, there is contained a hinge 42 which is best seen in FIG. 5. This hinge 42 mates with the protrusions 29 extending perpendicularly from the pair of posts 28 contained in the base 20 of the adaptor 28 cap assembly 10, as seen in FIG. 6. Also, the distal side of the outer gasket 45 contains a pair of locking members 48 which mate with the ball 32 of the base 20, so that when the outer gasket is flipped into its closed position (as seen in FIG. 7 or FIG. 1), the locking members mate with the ball 32, as best seen in FIG. 4.

Furthermore, the under or distal side of the outer gasket contains a sealing assembly which is comprised of three members. These are the cylindrical portion 50 of outer gasket 45 which extends distally from the flat undersurface 52 of the outer gasket 45. This cylindrical portion 50 is better seen in FIGS. 1, 3 and 5. There is also contained an insert 54 which is placed into the open cylindrical chamber 56 of the cylindrical portion of outer gasket 45. This insert 54 is similarly cylindrical and contains elastomeric gasket 49 which abuts the opening 46 contained in the outer gasket 45. This elastomeric material is best seen in FIGS. 1 and 2. The opening 46 contained in the gasket 45 is such that the elastomeric gasket 49 allows instruments roughly the size of the opening 46 of outer gasket 45 to be placed therein, with a seal maintained around the diameter of that instrument.

Finally, contained in the assembly 40 on the underside of the outer gasket 45 is a cap 58. This cap 58 contains a proximal end 60 which maintains the insert 54 fixedly within the cylindrical opening 56 of the cylindrical portion 50. Also, this cap 58 contains a flange 62 so that a seal is maintained between the cap 58 and the cylindrical portion 50 of the outer gasket 45. Thus, sealing is maintained in the chamber created by outer gasket 45, insert 54 and cap 58. Finally, cap 58 contains a distal trapezoidally shaped cylinder 64 which creates an opening 66 on the distal side of the outer gasket 45 identical to the dimension of in the opening 46 on the proximal side 68 of the outer gasket 45, to create a seal therebetween. This reduced sized opening 66 is seated in the opening 26 contained in the base of the adaptor cap assembly 10.

The invention described by this adaptor cap assembly 10 contains a number of different facets. Typically, the surgeon inserts a trocar 100 (without the adaptor cap attached) into the abdomen of the patient. This is done by inserting the obturator 105 into the cannula 110 so that the obturator handle 107 mates with the cannula handle 112. Thereafter, the sharpened obturator tip 115 of the obturator handle 107 pierces the abdominal wall; after insertion, the safety shield 109 as seen in FIG. 7 covers the sharpened obturator tip 107, to avoid injury to the abdominal cavity. Once the cannula 110 is in place, the obturator handle 107 is removed, and then a 10 mm opening in the cannula handle 112 and through the cannula 110 is exposed to the user. Of course, a seal is maintained by the lever arm 116 contained on the cannula handle 112, as is well known in the art.

Thereafter, the surgeon may attach the adaptor cap assembly 10 of this invention as described above. Flanges 22 and tabs 24 mate with walls 114 of cannula handle 112. Adaptor cap assembly 10 may be placed in the open position as seen in FIG. 7 or in the closed position as seen in FIG. 7a. This will depend entirely on the type of device which the surgeon is seeking to use within the cannula 110 contained in the cannula handle 112. If there is an instrument of a smaller dimension than the dimensional opening of the cannula 112, the adaptor cap assembly is placed as in FIG. 7a, with the ball 32 mating with the locking members 48 of the outer gasket 45 (FIG. 4). A smaller diameter instrument is then sealed against the seal 49 of the outer gasket 45 when placed through opening 46, and maintained fixedly within the center of the cannula 112 by the openings 66 and 26 in the cap 58 placed against the base 20 respectively, of the adaptor cap assembly 10.

On the other hand, if the surgeon desires to use a larger diameter instrument the surgeon merely flips the end 69 of the outer gasket 45 with a thumb, so that arms 48 disengage from the locking ball 32 contained on the base 20 of the mechanism. Thereafter, the adaptor cap assembly is placed in the position as seen in FIG. 7, so that the detent 44 contained on the proximal side 68 of the outer gasket 45 is placed distally within the slot 30 contained in the base 20 of the adaptor cap assembly 10, locking outer gasket 45 in place. Thereafter, the surgeon can use either assembly with impunity, depending on the size of the instrument.

In this way, the adaptor cap assembly 10 provides safe, quick and reliable sealing for all sizes of instruments, even instruments smaller than the dimensional opening of the trocar cannula. It is to be understood, therefore, that the invention described herein is disclosed by the appended claims, and their equivalents.

What is claimed is:

1. A trocar, containing a cannula handle, and a cannula extending therefrom, said cannula having a internal cylindrical opening and said cannula handle having an opening at a proximal end; and an adaptor cap assembly comprising:

a base having a cylindrical opening; and an outer gasket assembly attached to said base and able to be rotated with respect thereto, said outer gasket assembly having a cylindrical opening generally smaller than the cylindrical opening of said base; and said outer gasket assembly capable of being matedly seated within the cylindrical opening of said base;

wherein said outer gasket assembly contains an underside which protrudes through said base.

2. The trocar of claim 1 wherein said outer gasket assembly comprises an outer gasket containing a gasket attached thereto such that said gasket seals around an instrument having a diameter smaller than the diameter of said opening in said base.

3. The trocar of claim 1 wherein said outer gasket assembly is capable of locking to said base.

4. The trocar of claim 1 wherein said outer gasket is capable of locking to said base in a position wherein said opening in said outer gasket assembly is aligned with said opening in said base.

5. The trocar of claim 4 wherein said locking is accomplished by a locking mechanism contained partly on said base and partly on said outer gasket assembly.

6. The trocar of claim 5 wherein said locking mechanism comprises a pair of locking arms.

7. The trocar of claim 6 wherein said locking mechanism further comprises a mating ball, said locking arms capable of locking around said ball.

8. A trocar, containing a cannula handle, and a cannula extending therefrom, said cannula having a internal cylindrical opening and said cannula handle having an opening at a proximal end; and an adaptor cap assembly comprising:

a base having a cylindrical opening; and an outer gasket assembly attached to said base and able to be rotated with respect thereto, said outer gasket assembly having a cylindrical opening generally smaller than the cylindrical opening of said base; and said outer gasket assembly capable of being matedly seated within the cylindrical opening of said base;

wherein said outer gasket assembly is capable of locking to said base in a position wherein said opening in said outer gasket assembly is not aligned with said opening in said base.

9. The trocar of claim 8 wherein said locking is accomplished by a locking mechanism, said locking mechanism contained partly on said base and partly on said outer gasket assembly.

10. The trocar of claim 9 wherein said locking mechanism comprises a detent, and said detent mating with a slot contained on one of said outer gasket assembly and said base.

11. In a trocar, containing a cannula handle, and a cannula extending therefrom, said cannula having a internal cylindrical opening and said cannula handle having an opening at a proximal end, an adaptor cap assembly comprising:

a base having a cylindrical opening; and an outer gasket assembly attached to said base and rotatable with respect thereof;

said outer gasket assembly having a cylindrical opening generally smaller than the cylindrical opening of said base, said outer gasket assembly capable of being matedly seated within the cylindrical opening of said base;

wherein said outer gasket assembly comprises:

an outer gasket containing an opening and a cap containing an opening, said cap opening generally the same size as the opening in said outer gasket, and said cap opening containing a circularly arrayed side wall, said side wall capable of seating within the opening of said base when said outer gasket assembly is matedly seated within the opening of said base.

12. A trocar, containing a cannula handle, and a cannula extending therefrom, said cannula having a internal cylindrical opening and said cannula handle having an opening at a proximal end; and an adaptor cap assembly comprising:

a base having a cylindrical opening; and an outer gasket assembly attached to said base and rotatable with respect thereto, said outer gasket assembly having a cylindrical opening generally smaller than the cylindrical opening of said base, wherein said outer gasket assembly locks to said base by a locking mechanism contained partly on said base and partly on said outer gasket assembly; and wherein said locking mechanism comprises at least a pair of locking arms;

wherein said outer gasket assembly contains an underside which protrudes through said base.

13. In a trocar, containing a cannula handle, and a cannula extending therefrom, said cannula having a internal cylindrical opening and said cannula handle having an opening at a proximal end, an adaptor cap assembly comprising:

a base having a cylindrical opening; and an outer gasket assembly attached to said base and able to be rotated with respect thereto, said outer gasket having a cylindrical opening generally smaller than the cylindrical opening of said base; and said outer gasket assembly capable of being matedly seated within the cylindrical opening of said base;

wherein said outer gasket assembly is capable of locking to said base in a position wherein said opening in said outer gasket assembly is not aligned with said opening in said base.

14. The adaptor cap assembly of claim 13 wherein said locking mechanism comprises a detent, and said detent mating with a slot contained on one of said outer gasket assembly and said base.

* * * * *